(12) United States Patent
Rao et al.

(10) Patent No.: US 10,329,592 B2
(45) Date of Patent: *Jun. 25, 2019

(54) SIGNAL PEPTIDE, L-GLUTAMIC ACID SYNTHESIZED USING KONJAC FLOUR AND METHODS OF USING SAME

(71) Applicant: Jiangnan University, Wuxi (CN)

(72) Inventors: Zhiming Rao, Wuxi (CN); Junxian Zheng, Wuxi (CN); Meijuan Xu, Wuxi (CN); Taowei Yang, Wuxi (CN); Xian Zhang, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/736,489

(22) PCT Filed: Nov. 23, 2015

(86) PCT No.: PCT/CN2015/095285
§ 371 (c)(1),
(2) Date: Dec. 14, 2017

(87) PCT Pub. No.: WO2017/088094
PCT Pub. Date: Jun. 1, 2017

(65) Prior Publication Data
US 2018/0245114 A1  Aug. 30, 2018

(51) Int. Cl.
| | | |
|---|---|---|
| *C12N 15/09* | (2006.01) |
| *C12P 13/14* | (2006.01) |
| *C12N 15/77* | (2006.01) |
| *C12N 9/24* | (2006.01) |
| *C12N 9/88* | (2006.01) |
| *C12N 15/62* | (2006.01) |
| *C12P 13/00* | (2006.01) |
| *C12R 1/13* | (2006.01) |

(52) U.S. Cl.
CPC .......... *C12P 13/14* (2013.01); *C12N 9/2491* (2013.01); *C12N 9/88* (2013.01); *C12N 15/62* (2013.01); *C12N 15/77* (2013.01); *C12P 13/005* (2013.01); *C07K 2319/02* (2013.01); *C12R 1/13* (2013.01); *C12Y 302/01025* (2013.01); *C12Y 401/01015* (2013.01)

(58) Field of Classification Search
None
See application file for complete search history.

(56) References Cited

U.S. PATENT DOCUMENTS

| | | | |
|---|---|---|---|
| 2018/0245114 A1* | 8/2018 | Rao | C12N 15/77 |
| 2018/0258385 A1* | 9/2018 | Rao | C12N 1/20 |

OTHER PUBLICATIONS

Tanaka et al. (Biosci., Biotech. & Biochem., vol. 71 (1), 2009, pp. 109-116).*

* cited by examiner

*Primary Examiner* — Hope A Robinson
(74) *Attorney, Agent, or Firm* — Na Xu; IPro, PLLC

(57) ABSTRACT

The present invention relates to application of a novel signal peptide in L-glutamate and its derivatives production from konjac powder, which belongs to the field of gene engineering, enzyme engineering and metabolism engineering. The signal peptide which mediated secretion of β-mannanase was invented, and the recombinant strain with this signal peptide had advantages on utilizing konjac powder to produce related products, and its utilization efficiency of konjac powder, production efficiency, and yield were higher than other signal peptides. The recombinant strain possessing this new signal peptide had advantages on utilizing cheaper konjac powder as substrate to lower the process costs on L-glutamic acid and its high-value-added products.

1 Claim, No Drawings
Specification includes a Sequence Listing.

SIGNAL PEPTIDE, L-GLUTAMIC ACID SYNTHESIZED USING KONJAC FLOUR AND METHODS OF USING SAME

BACKGROUND OF THE INVENTION

Field of the Invention

The invention relates to application of a novel signal peptide in L-glutamate and its derivatives production from konjac powder, which belongs to the field of gene engineering, enzyme engineering and metabolism engineering.

Description of the Related Art

Konjac powder, which made from non-grain crops konjac, is rich in konjac mannan. Konjac is mainly distributed in China, Japan, Burma, Vietnam, Indonesia, Southeast Asia and Africa and other regions. Konjac, which belongs to Araceae, is rich in resources, and can be intercropped with food crops, or grown in silt or beaches, thus it doesn't compete arable land with crops, and can be further developed. According to related reports, Yunnan, Guizhou, Sichuan, Hubei and Hunan, Shanxi and other places in the West China are suitable for cultivation of Konjac, there have been certain cultivation scale, and the cultivation area of konjac have reached 410,000 acres in Hubei province. Currently, konjac powder is mainly used for part of food, and its hydrolyzed oligosaccharides can be used as functional food, and its application has not been extensively developed. Konjac, as a main dietary fiber containing food, is identified as one of the top ten health foods by WHO. However, human cannot digest glucomannan from konjac powder, so its daily intake is less than 10 g. A large surplus of konjac can be used for development and utilization. Most microorganisms cannot directly utilize konjac powder, so it has good application prospects to adapt microbes to ferment cheaper konjac powder as a carbon source to produce high-value-added products.

The *Brevibacterium tianjinese* SW07-1 which has been patented and preserved by our lab could only utilize glucose as the main carbon source to produce L-glutamic acid, and konjac powder can't be use as its direct main carbon source.

L-glutamic acid is mainly used for production of monosodium glutamate, spices, as well as salt substitutes, nutritional supplements and biochemical reagents. By means of genetic and metabolic engineering technique, the high yield strain can also ferment konjac powder as carbon source to produce L-glutamic acid. It has certain reference application value for simplifying the production process of L-glutamic acid and saving the production cost.

L-glutamic acid can be further catalyzed by glutamate decarboxylase (GAD, EC 4.1.1.15) to produce γ-aminobutyric acid and carbon dioxide. γ-amino butyric acid (GABA) is a kind of non-protein amino acids naturally occurring in some living things. γ-amino butyric acid acts as an important inhibitory neurotransmitter and has several physiological functions like antidepression, blood pressure reducing, calming, memory enhancement, hormone secretion, generative enhancement, abirritation, and it is extensively applied in the field of food, animal feed, and medicine.

The strain which can utilize cheap konjac powder as a carbon source to produce L-glutamic acid is further improved to produce high value added γ-amino butyric acid through genetical and metabolic engineering technology, and it has considerable prospects to save food and reduce production costs.

DETAILED DESCRIPTION

By taking advantage of genetical engineering, the signal peptide of β-mannanase was deleted from itself first and replaced by 12 new ones from Sec and Tat secreting pathway from *Corynebacterium glutamicum* and *Bacillus subtilis* respectively. The effects of signal peptides replacement on β-mannanase secretion were compared among different strains with high L-glutamic acid production. Finally, the codon of a β-mannanase signal peptide designated as MSP (Mannase Signal Peptide) was optimized which was found to be a new signal peptide with a better enzyme secretion ability.

The first goal of the present invention is to provide a signal peptide, comprises one of the characteristics described as following (a) to (d) items:

(a) the nucleotide sequence of it is the same as the sequence set forth in SEQ ID NO.1;

(b) the nucleotide sequence of it contains the sequence set forth in SEQ ID NO.1, and the signal peptide has an activity of a Mannase signal peptide;

(c) the nucleotide sequence of it contains a sequence which has at least one base of deletion, replacement or addition, compared with the sequence set forth in SEQ ID NO:1; and the signal peptide has an activity of a Mannase signal peptide;

(d) the nucleotide sequence of it is from *Bacillus subtilis*, and could hybridize with the sequence set forth in SEQ ID NO:1 under stringency conditions; and the signal peptide has a activity of Mannase signal peptide.

The second purpose of the present invention is to provide a genetically engineered strain which can utilize both konjac powder and glucose, the genetically engineered strain expresses a β-mannanase fused with said signal peptide whose nucleotide sequence is set forth in SEQ ID NO:1; after the signal peptide is fused with β-mannanase, the expression vector of the fusion gene is introduced to host cell.

In one embodiment of the present invention, the gene of the β-mannanase is derived from *Bacillus subtilis*, but not restricted to *Bacillus subtilis*.

In one embodiment of the present invention, the gene of the β-mannanase is derived from *Bacillus subtilis* CCTCC M 209200, the nucleotide sequence is shown in SEQ ID NO:3.

In one embodiment of the present invention, the expression vector is pXMJ19, but not restricted to pXMJ19.

In one embodiment of the present invention, the host strain is *Brevibacterium tianjinese*, but not restricted to *Brevibacterium tianjinese*.

In one embodiment of the present invention, the host strain is *Brevibacterium tianjinese* SW07-1 (Published in ZL201310196284.1).

In one embodiment of the present invention, the genetically engineered strain can express glutamate decarboxylase.

In one embodiment of the present invention, the the expression of glutamate decarboxylase gene is connecting the glutamate decarboxylase gad to the vector pDXW10, and introducing the expression vector to host cell.

In one embodiment of the present invention, the glutamate decarboxylase is derived from *Lactobacillus plantarum*, but not restricted to *Lactobacillus plantarum*.

In one embodiment of the present invention, the glutamate decarboxylase gene is derived from *Lactobacillus plantarum* CCTCC M 209102 (namely *Lactobacillus plantarum* GB01-21), the accession number on NCBI is No. JN248358.

In one embodiment of the present invention, the genetically engineered strain is named of SW07-1/pMSPman, and it was constructed by the following method: β-mannanase of *Bacillus subtilis* is fused with the signal peptide, then the fused gene is inserted into pXMJ19 expression vector to form recombinant plasmid named pXMJ19-MSPman, finally the recombinant plasmid is translated to *Brevibacterium tianjinese* SW07-1 to get genetically engineered strain named SW07-1/pMSPman.

In one embodiment of the present invention, the genetically engineered strain is SW07-1/pMSPman-pgad, which can express glutamate decarboxylase of *Lactobacillus plantarum* on the base of SW07-1/pMSPman.

The third purpose of the present invention is to provide a method of utilizing konjac powder to produce L-glutamic acid or γ-aminobutyric acid, which uses genetically engineered strain to ferment the konjac powder as a main carbon source.

In one embodiment of the present invention, konjac powder and glucose are used as mixed carbon source. The effect of glucose is to accelerate the cell growth during early fermentation phase, konjac powder is used to induce the secretion of β-mannanase which in turn hydrolyzed konjac powder to provide effective carbon source to produce related products.

In one embodiment of the present invention, the fermentation medium contains 10 g/L konjac powder and 30 g/L glucose, and konjac powder is used as a feed in the late fed-batch fermentation process, and the total feed amount of konjac powder is 80 g/L.

The forth purpose of the present invention is to provide an expression vector containing the signal peptide.

In the present invention, a new signal peptide which mediated secretion of β-mannanase is invented, and the recombinant strain with this signal peptide has advantages on utilizing konjac powder to produce related products, and its utilization efficiency of konjac powder, production efficiency, and yield are higher than other signal peptides. The recombinant strain possessing this new signal peptide has advantages on utilizing cheaper konjac powder as substrate to lower the process costs on L-glutamic acid and its high value-added products. The present invention is also suitable for other *Brevibacterium tianjinese* as host cell, and can improve the ability to utilize konjac powder to synthesis L-glutamic acid or γ-aminobutyric acid.

In the present invention, based on the strains with high L-glutamic acid yield, the new constructed strain possessing signal peptide invented in this invention which mediated β-mannanase secretion can utilize mixed carbon source of konjac powder and glucose to produce L-glutamic acid. SW07-1/pMSPman is constructed in this invention, after fermenting for 48 hours in a 5 L bioreactor, the yield of L-glutamic acid and the enzyme activity of β-mannanase can reach 65±1.2 g/L and 1210±4.6 U/mL respectively.

In the present invention, the recombinant SW07-1/pMSPman-pgad which could express glutamate decarboxylase of *Lactobacillus plantarum* is constructed based on SW07-1/pMSPman. The recombinant SW07-1/pMSPman-pgad can utilize konjac powder and glucose as mixed carbon source to produce γ-aminobutyric acid. The production of γ-aminobutyric acid and the enzyme activity of β-mannanase can reach 45.5±0.9 g/L and 1203±6.8 U/ml by the fermentation with recombinant SW07-1/pMSPman-pgad in a 5 L bioreactor for 96 hours after process optimization. The initial culture medium contains 10 g/L konjac powder, 30 g/L glucose, and konjac powder is used as a feed in the later fed-batch fermentation process, and the total feed amount of konjac powder is 80 g/L.

EXAMPLES

Material and Methods:

Primers: The fusion primers for the signal peptide and target gene were designed according to the related gene sequences published on NCBI.

The strain construction method: The chromosome DNA was extracted from the related strains as templates, and the PCR was run according to the preliminary design of the primers, amplification conditions and system. The PCR products were purified and recovered by using gel extraction kit, and the recovered products concentration were determined by agarose gel electrophoresis of nucleic acid. The related expression vector and purified PCR products were double-enzyme digested by using the same restriction endonuclease, the enzyme-digested products were tested by agarose gel electrophoresis and recovered by gel extraction kit, and its concentration was determined by ultra-microspectrophotometer. Mixed the enzyme-digested products and the PCR products, and connected them by T4 DNA ligase overnight. The recombinant vector was introduced to *Escherichia coli* BL21 by CaCl$_2$) transformation method, finally *Escherichia coli* BL21 containing recombinant plasmid was constructed. The plasmid was extracted and validated by single and double enzyme-digestion and PCR, finally it was introduced to related strain by electrotransformation method. At last, the recombinant strain was stored at −70° C. with 15% glycerol.

The recombinant strain was inoculated into fresh LB+0.5% Glucose liquid culture medium with 1% inoculum concentration. Then it was transferred to fermentation culture medium which contained konjac powder and glucose as substrate at next day. The fermentation broth was collected at the late growth phase and the concentration of amino acids (L-glutamic acid and related amino acids) were determined by automatic amino acids analyzer. The fermentation medium contained enough nutritional ingredient that was suitable for microorganism growth, and had been optimized.

Example 1: The Primers Design for Signal Peptide Tadem β-Mannanase

P1 and P2 for signal peptide tandem β-mannanase were designed according to the related gene sequences and β-mannanase gene published on NCBI. The sequences of P1 and P2 were shown in SEQ ID NO:4 and SEQ ID NO:5 respectively.

```
P1: pMSPmadHindIIIF
5'-CCCAAGCTTATGTTCAAGAAGCACACCATCTCCCTGCTGATCATCTT

CCTGCTGGCTTCCGCTGTTCTGGCTAAGCCAATCGAGGCTCATACTGTGT

CGCCTGTGAATC-3'

P2: pMSPmanBamHIR
5'-CGCGGATCCTTACTCAACGATTGGCGTTA-3'
```

Example 2: Clone and Replacement of Signal Peptide of β-Mannanase

The chromosome DNA was extracted from *B. subtilis* CCTCC M 209200 as templates.

The PCR primers for signal peptide tandem β-mannanase were designed according to the β-mannanase sequence published on NCBI. MSP (Mannase signal peptide) tandem β-mannanase was achieved by using the chromosome DNA of *B. subtilis* CCTCC M 209200 as template and P1/P2 as primers. The codon of MSP was optimized and whose DNA sequence was shown in SEQ ID NO:1, and the sequence of β-mannanase without signal peptide was shown in SEQ ID NO:3. PCR amplification system (50 μL): 1 μL template, 0.5 μL primers, 4 μL dNTP Mix, 5 μL 10×Ex Taq Buffer, 38.5 μL sterile ddH$_2$O, 0.5 μL Ex Taq DNA polymerase. PCR reaction conditions: Pre-denaturation at 94° C. for 5 minutes for one round; sequential denaturation at 94° C. for 30 seconds, annealing at 56° C. for 30 seconds, and elongation at 72° C. for 90 seconds for 30 rounds; elongation at 72° C. for 10 minutes for one round; 4° C. for 40 minutes for one round. The annealing and elongation temperature should be adjusted according to different primers and genes. PCR products were purified and recovered by gel extraction kit, the purity of products was determined by electrophoresis. The recovered products were stored in 1.5 mL centrifuge tubes at −20° C.

Example 3: The Construction of Recombinant Vector pXMJ19-MSPman

Joined the recovered PCR products in embodiment 2 and cloning vector pMD18-T. The ligation system: 5 μL solution, 4.8 μL target gene, 0.2 μL pMD18-T. The ligation between these two DNA molecules was carried out at 16° C. overnight. The recombinant plasmid was introduced to *E. coli* JM109. Then, *E. coli* JM109 was spread on LB plates containing 100 ug/mL ampicillin and cultured at 37° C. overnight. Individual clonal was picked and inoculated to liquid LB culture medium containing 100 ug/mL ampicillin. After cultivation at 37° C. overnight, the plasmid was extracted outside and named pMD18-T-MSPman. When the validation was successful through PCR and enzyme-digestion, the strain was stored at 70° C. with 15% glycerol. pMD18-T-MSPman and pXMJ19 were cut by HindIII and BamHI, the products were recovered by gel extraction kit and joined together. Finally, recombinant plasmid called pXMJ19-MSPman was achieved. The validation of the recombinant plasmids was successful through PCR and enzyme-digestion.

Example 4: The Electro-Transfection of *Brevibacterium tianjinese* SW07-1 with Recombinant Vector pXMJ19-MSPman

*Brevibacterium tianjinese* SW07-1 was picked up and inoculated into flasks with 10 mL LB liquid culture medium, and was cultured at 30° C. overnight. 100 μL broth was taken from flask and inoculated into culture medium for competent cell, and cultured at 30° C. for 4 hours until OD562 reached about 0.9. The broth was centrifuged in sterile tubes and the supernatant was discarded. Then the pellets were resuspended and centrifuged with 10% glycerol for 3 times. Finally, the competent cells were divided into 1.5 mL centrifuge tubes equally, and 3 uL recombinant plasmid was added into those tubes. The competent cells with recombinant plasmid were subjected to an electric-transfection under the condition of 1800 V and 50 mS. Then the cells were inoculated into fresh LBG culture medium (Medium composition: 0.5% yeast extract, 1% peptone, 1% NaCl, 0.5% glucose), and placed into water bath at 46° C. for 6 minutes, then cultured at 30° C. for 3 hours. Finally, the cells were spread on plates containing chloromycetin and cultured at 30° C. for 64 hours. The single colony was picked and cultivated. Then, the plasmid of single colony was extracted and validated through enzyme-digestion and PCR. The positive recombinant strain was named SW07-1/pMSPman and stored at 70° C.

Example 5: The Determination of Enzyme Activity of β-Mannanase Secreted from Recombinant SW07-1/pMSPman 2.0 mL 5.0 g/L Locust bean gum substrate solution was added to tubes, then preheated the tubes at 65° C. for 10 minutes. 2.0 mL crude enzyme solution with appropriate concentration was added into tubes, and the reaction was carried out at 65° C. for 10 minutes. 5.0 mL DNS reagent was added immediately into tubes, then shook those tubes for a while. Place those tubes into boring water for 10 minutes, then use ice water to cool down tubes. Water was added to make the liquid volume in the tubes to be 10.0 mL, then shook those tubes for a while. 2.0 mL water was used to replace the crude enzyme as control group. The absorbance at 540 nm was measured to calculate the enzyme activity of β-mannanase according to mannose standard curve. The definition of enzyme activity unit: One unit of enzyme activity of β-mannanase was equal to the enzyme amount needed to produce 1 μmol reducing sugar per minute.

Example 6: Fermentation of Recombinant SW07-1/pMSPman

The seed of recombinant SW07-1/pMSPman was inoculated to konjac powder medium under the cultivation condition of 30° C. and 500 r/min. 48 hours later, the concentration of γ-aminobutyric acid reached 65±1.2 g/L, and the enzyme activity of β-mannanase was 1210±4.6 U/mL.

Konjac Powder Medium (g/L):

The initial culture medium contains 10 g/L konjac powder, 30 g/L glucose, 3 g/L corn steep liquor, 20 g/L (NH$_4$)$_2$SO$_4$, 1.5 g/L KH$_2$PO$_4$.3H$_2$O, 0.8 g/L MgSO$_4$.7H$_2$O, 0.02 g/L FeSO$_4$.7H$_2$O, 0.02 g/L MnSO$_4$.H$_2$O, 5.5 g/L urea, 200 ug/L VB1, and the pH of the liquid medium was between 7.0 to 7.2; After fermenting for 12 hours, konjac powder was fed into broth, and the total feed amount of konjac powder was 80 g/L.

Control Group:

Similar fermentation process of embodiment 1-6 was employed to cultivate the control strain which only differed in signal peptide shown in SEQ ID NO:1 that was replaced by the original one of β-mannanase which was shown in SEQ ID NO:2. The concentration of γ-aminobutyric acid was only 43±3.2 g/L, and the enzyme activity of β-mannanase was only 867±7.8 U/mL in control group.

Similar fermentation process of embodiment 1-6 was employed to cultivate the control strain which only differed in signal peptide shown in SEQ ID NO: 1 that was replaced by signal peptide PS (SEQ ID NO:6) of surface proteins from *Corynebacterium glutamicum* or by signal peptide AE (SEQ ID NO:7) of α-amylase from *Bacillus subtilis*. The concentration of γ-aminobutyric acid was 20±1.2 g/L and 15±2.4 g/L respectively, and the enzyme activity of β-mannanase was 480±3.6 U/mL and 378±5.7 U/mL respectively in control groups.

To sum up, by taking advantage of signal peptide (SEQ ID NO:1) of this invention, the capability of utilizing konjac powder to produce products of the recombinant strain was significantly improved than by other signal peptides with 51%~333% increase in production and 39.6%~220% increase in the enzyme activity of β-mannanase.

Example 7: The Determination of L-Glutamic Acid of Recombinant SW07-1/pMSPman L-glutamic acid in the fermentation broth was first determined by a biosensor, then its accurate concentration was determined by an amino acids analyzer.

Example 8: The Primer Design for Construction of Recombinant SW07-1/pMSPman-Pgad Based on the inventors' former patent (Publication Number: CN103243128A), the designed primer p1 and p2 were shown below in SEQ ID NO:8 and SEQ ID NO:9, respectively.

```
p1: pgadEcoRIF
5'-CGGAATTCATGGACCAGAAGCTGTTAAC-3' p2: pgadSacIR
5'-CCGAGCTCTTACAGTGTGTTTAAAGCTGTT-3'
```

Example 9: The Construction of Recombinant Plasmid pDXW10-Gad

Gad gene containing restriction enzyme cutting site of EcoRI and SacI was obtained by using *Lactobacillus plantarum* GB01-21 (CCTCC M 209102) chromosome as template and primers designed in embodiment 8 and purified by related kits. The purified PCR products and expression vector pDXW10 were cut by EcoRI and SacI, then the products were recovered by gel extraction kit. Join the recovered products at 16° C. overnight. The recombinant plasmid was introduced to *E. coli* JM109, then spread the cells on the LB plates containing 100 ug/mL kanamycin, and cultivated at 37° C. overnight. Single colony was picked up and inoculated to 10 mL LB liquid culture medium containing 100 ug/mL kanamycin. Culture the cells at 37° C. overnight, the extract the plasmid named pDXW10-gad out of broths. After the validation was passed through PCR and enzyme-digestion, the strain was stored at −70° C.

Example 10: The Recombinant Plasmid pDXW10-Gad was Electro-Transfected to SW07-1/pMSPman SW07-1/pMSPman was used as an original strain for electro-transfection, and the antibiotic screening marker was kanamycin. Embodiment 4 was used as a reference. Finally, recombinant strain SW07-1/pMSPman-pgad was screened out.

Example 11: The Determination of Enzyme Activity of Glutamate Decarboxylase from Recombinant SW07-1/pMSPman-Pgad Prepare MacIlvaine buffer system for substrate solution (0.2 mol/L, pH 4.8, containing 0.1 mmol/L PLP, and 0.4 mol/L L-sodium glutamate), then 200 μL of substrate solution was mixed with 100 μL of enzyme solution for reaction at 30° C., then the mixture was placed in ice bath, finally 200 μL 0.2 mol/L borate buffer (pH 9.0) was added to end the reaction. 1.0 mL 6% phenol solution and 400 μL sodium hypochlorite solution were added into the tubes, and shook the tubes for a while, then put the tubes into boiling water for 10 minutes. Cool down the tubes immediately in ice bath and the color appeared. One enzyme activity unit was equal to the enzyme amount needed for production of 1 umol GABA per minute.

Example 12: The Fermentation of Recombinant SW07-1/pMSPman-Pgad

The seed of recombinant SW07-1/pMSPman-pgad was inoculated to konjac powder medium under the cultivation condition of 30° C. and 500 r/min. 48 hours later, the concentration of γ-aminobutyric acid reached 45.5±0.9 g/L, and the enzyme activity of β-mannanase was 1203±6.8 U/mL.

Konjac Powder Medium (g/L):

The initial culture medium contains 10 g/L konjac powder, 30 g/L glucose, 3 g/L corn steep liquor, 5.5 g/L urea, 1.5 g/L $KH_2PO_4 \cdot 3H_2O$, 0.8 g/L $MgSO_4 \cdot 7H_2O$, 0.02 g/L $MnSO_4 \cdot H_2O$, 0.02 g/L $FeSO_4 \cdot 7H_2O$, 1 $2 \times 10^{-4}$ g/L VB1, and the pH of the liquid medium was between 7.0 to 7.2; After fermenting for 12 hours, konjac powder was fed into broth, and the total feed amount of konjac powder was 80 g/L.

Control Group:

Similar fermentation process was employed to cultivate the control strain which was only differ in signal peptide that shown in SEQ ID NO:1 was replaced by the original one of β-mannanase which was shown in SEQ ID NO:2. The concentration of γ-aminobutyric acid was 33±2.1 g/L, and the enzyme activity of β-mannanase was 850±5.8 U/mL in control group.

Similar fermentation process was employed to cultivate the control strain which was only differ in signal peptide that shown in SEQ ID NO: 1 was replaced by signal peptide PS (SEQ ID NO:6) of surface proteins from *Corynebacterium glutamicum* or by signal peptide AE (SEQ ID NO:7) of α-amylase from *Bacillus subtilis*. The concentration of γ-aminobutyric acid was 14±1.3 g/L and 10±1.8 g/L respectively, and the enzyme activity of β-mannanase was 452±2.6 U/mL and 330±4.6 U/mL respectively in control groups.

To sum up, by taking advantage of signal peptide (SEQ ID NO:1) of this invention, the capability of utilizing konjac powder to produce products of the recombinant strain was significantly improved than other signal peptides with 38%~355% increment in production and 41.5%~264% increment in the enzyme activity of β-mannanase.

Example 13: The Determination of γ-Aminobutyric Acid from Fermentation Broth of Recombinant SW07-1/pMSPman-PargI Amino acid analyzer was used to determine the precise concentration of γ-aminobutyric acid from fermentation broth.

While the present invention has been described in some detail for purposes of clarity and understanding, one skilled in the art will appreciate that various changes in form and detail can be made without departing from the true scope of the invention.

What is claimed is:

1. A signal peptide, encoded by a nucleotide sequence comprising:
   a non-naturally occurring nucleotide sequence set forth in SEQ ID NO: 1,
   wherein the signal peptide is a mannase signal peptide.

* * * * *

SEQUENCE LISTING

<160> NUMBER OF SEQ ID NOS: 9

<210> SEQ ID NO 1
<211> LENGTH: 78
<212> TYPE: DNA
<213> ORGANISM: Artificial Sequence
<220> FEATURE:
<223> OTHER INFORMATION: Synthetic DNA

<400> SEQUENCE: 1

```
atgttcaaga agcacaccat ctccctgctg atcatcttcc tgctggcttc cgctgttctg    60
gctaagccaa tcgaggct                                                  78
```

<210> SEQ ID NO 2
<211> LENGTH: 78
<212> TYPE: DNA
<213> ORGANISM: Artificial Sequence
<220> FEATURE:
<223> OTHER INFORMATION: Synthetic DNA

<400> SEQUENCE: 2

```
atgtttaaga acatacgat ctctttgctc attatatttt tacttgcgtc tgctgttta     60 gcaaaaccaa ttgaagcg                                                  78
```

<210> SEQ ID NO 3
<211> LENGTH: 1014
<212> TYPE: DNA
<213> ORGANISM: Artificial Sequence
<220> FEATURE:
<223> OTHER INFORMATION: Synthetic DNA

<400> SEQUENCE: 3

```
atgcatactg tgtcgcctgt gaatcctaat gcccagcaga caacaaaaac agtgatgaac    60
tggcttgcgc acctgccgaa ccgaacggaa aacagagtcc tttccggagc gttcggaggt   120
tacagccatg acacattttc tatggctgag gctgatagaa tccgaagcgc cactgggcaa   180
tcgcctgcta tttatggctg cgattatgcc agaggatggc ttgaaacagc aaatattgaa   240
gattcaatag atgtaagctg caacggcgat ttaatgtcgt attggaaaaa tggcggaatt   300
ccgcaaatca gtttgcacct ggcgaaccct gcttttcagt cagggcattt taaaacaccg   360
attacaaatg atcagtataa aaaaatacta gattcttcaa cagtagaagg aaggcggcta   420
aatgccatgc tcagcaaaat tgctgacgga cttcaagagt tggagaacca aggtgtgcct   480
gttctgttca ggccgctgca tgaaatgaac ggcgaatggt tttggtgggg actcacatca   540
tataaccaaa aggataatga agaatctct ctatataaac agctctacaa gaaaatctat    600
cattatatga ccgacacaag aggacttgat catttgattt gggtttactc tcccgacgcc   660
aaccgagatt ttaaaactga tttttacccg ggcgcgtctt acgtggatat tgtcggatta   720
gatgcgtatt ttcaagatgc ctactcgatc aatggatacg atcagctaac agcgcttaat   780
aaaccatttg cttttacaga agtcggcccg caaacagcaa acggcagctt cgattacggc   840
ctgttcatca atgcaataaa acaaaaatat cctaaaacca tttactttct ggcatggaat   900
gatgaatgga gcgcagcagt aaacaagggt gcttcagctt tatatcatga cagctggaca   960
ctcaacaagg gagaaatatg gaatgatgat tctttaacgc caatcgttga gtaa         1014
```

<210> SEQ ID NO 4
<211> LENGTH: 109
<212> TYPE: DNA
<213> ORGANISM: Artificial Sequence
<220> FEATURE:
<223> OTHER INFORMATION: Synthetic DNA

<400> SEQUENCE: 4

```
cccaagctta tgttcaagaa gcacaccatc tccctgctga tcatcttcct gctggcttcc      60
gctgttctgg ctaagccaat cgaggctcat actgtgtcgc ctgtgaatc                 109
```

<210> SEQ ID NO 5
<211> LENGTH: 29
<212> TYPE: DNA
<213> ORGANISM: Artificial Sequence
<220> FEATURE:
<223> OTHER INFORMATION: Synthetic DNA

<400> SEQUENCE: 5

```
cgcggatcct tactcaacga ttggcgtta                                        29
```

<210> SEQ ID NO 6
<211> LENGTH: 102
<212> TYPE: DNA
<213> ORGANISM: Artificial Sequence
<220> FEATURE:
<223> OTHER INFORMATION: Synthetic DNA

<400> SEQUENCE: 6

```
atgtttaaca accgtatccg cactgcagct ctcgctggtg caatcgcaat ctccaccgca      60
gcttctggcg tagctatccc agcattcgct caggagacca ct                        102
```

<210> SEQ ID NO 7
<211> LENGTH: 84
<212> TYPE: DNA
<213> ORGANISM: Artificial Sequence
<220> FEATURE:
<223> OTHER INFORMATION: Synthetic DNA

<400> SEQUENCE: 7

```
atgtttgcaa aacgattcaa aacctcttta ctgccgttat tcgctggatt tttattgctg      60
tttcatttgg ttctggcagg accg                                             84
```

<210> SEQ ID NO 8
<211> LENGTH: 28
<212> TYPE: DNA
<213> ORGANISM: Artificial Sequence
<220> FEATURE:
<223> OTHER INFORMATION: Synthetic DNA

<400> SEQUENCE: 8

```
cggaattcat ggaccagaag ctgttaac                                         28
```

<210> SEQ ID NO 9
<211> LENGTH: 30
<212> TYPE: DNA
<213> ORGANISM: Artificial Sequence
<220> FEATURE:
<223> OTHER INFORMATION: Synthetic DNA

<400> SEQUENCE: 9

```
ccgagctctt acagtgtgtt taaagctgtt                                       30
```